(12) United States Patent
Sato (10) Patent No.: US 7,047,795 B2
(45) Date of Patent: May 23, 2006

(54) ANALYZING INSTRUMENT, ANALYZING DEVICE, AND METHOD OF MANUFACTURING ANALYZING INSTRUMENT

(75) Inventor: Yoshiharu Sato, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 191 days.

(21) Appl. No.: 10/485,169

(22) PCT Filed: Jul. 30, 2002

(86) PCT No.: PCT/JP02/07767

§ 371 (c)(1),
(2), (4) Date: Jan. 29, 2004

(87) PCT Pub. No.: WO03/012421

PCT Pub. Date: Feb. 13, 2003

(65) Prior Publication Data

US 2004/0216516 A1    Nov. 4, 2004

(30) Foreign Application Priority Data

Aug. 1, 2001   (JP) ............................. 2001-234024

(51) Int. Cl.
  *G01N 27/26*   (2006.01)
  *G01N 33/49*   (2006.01)
(52) U.S. Cl. .................. 73/64.56; 422/82.02; 422/98; 204/400; 204/416; 29/428
(58) Field of Classification Search .............. 73/64.56; 422/82.02, 98; 204/400, 416; 29/428
See application file for complete search history.

(56) References Cited

U.S. PATENT DOCUMENTS 5,405,510 A    4/1995   Betts et al.

FOREIGN PATENT DOCUMENTS

| EP | 0 471 986 | 2/1992 |
| JP | 04-264246 | 9/1992 |
| JP | 5-164724 | 6/1993 |
| JP | 10-332626 | 12/1998 |
| JP | 2000-19147 | 1/2000 |

*Primary Examiner*—Daniel S. Larkin
(74) *Attorney, Agent, or Firm*—Hamre, Schumann, Mueller & Larson, P.C.

(57) ABSTRACT

An analyzing instrument (2) according to the present invention includes a capillary (6), a sample liquid inlet (42), and a liquid introduction controller for a controlled pattern of introduction of the sample liquid into the capillary. The capillary (6) preferably includes a common passage (60) and a plurality of individual passages (61–63) connecting to the common passage. In this arrangement, the liquid introduction controller selects for each of the individual passages (61–63) whether or not the sample liquid is introduced therein. The liquid introduction controller includes, for example, one or more through-holes (51–53) each communicating with e.g. the individual passages (61–63). The liquid introduction controller preferably selects for each of the individual passages (61–63) whether or not the sample liquid is introduced therein, by a selection whether or not the corresponding one of the through-holes (61–63) is opened or closed.

23 Claims, 11 Drawing Sheets

ANALYZING INSTRUMENT, ANALYZING DEVICE, AND METHOD OF MANUFACTURING ANALYZING INSTRUMENT

TECHNICAL FIELD

The present invention relates to a technology for analyzing a specific component in a sample liquid. The present invention is applicable to a technology for measuring blood glucose levels, for example.

BACKGROUND ART

As a common method of measuring blood glucose levels, an oxidation-reduction reaction is used. On the other hand, for handy measurement of the blood glucose levels at home and elsewhere, palm-size, portable blood glucose measuring devices are used widely. These handy-type blood glucose measuring devices make use of a disposable-biosensor which also serves as an enzyme reaction field. The blood glucose level measurement is made by supplying the blood to the biosensor.

Sensitivity of the individual biosensors can vary from one biosensor to another. The variation can be a result of difference in row materials, design changes in production lines and so on. Especially, when starting up the production line, due to needs for optimizing various conditions in the production line and selecting suitable materials, sensitivity variations among the produced sensors tend to be large. Further, when there are plural manufacturing plants or plural production lines of the biosensors, sensitivity variation among the plants or production lines can result. In preparation for these sensitivity variations, some blood glucose measuring devices incorporate a plurality of calibration curves. In addition, if the tester is capable of not only measuring the blood glucose level but also other values such as cholesterol level, a plurality of calibration curves must be prepared so that each kind of the components can be measured. In these cases, arrangements must be made so that the measuring device can recognize the sensitivity of each biosensor as well as information necessary for relating the calibration curve with the target component so that appropriate one of the calibration curves will be selected for a given measurement.

A first example for such selection of the calibration curve is that each of the plural calibration curves is given an identification code. The biosensor ID code will then be printed on boxes or instruction sheets of the biosensors. In this arrangement, the blood glucose measuring device incorporates a calibration curve selection program for example, which selects an appropriate calibration curve when the user makes an input to the blood glucose measuring device using buttons.

A second example for the selection of the calibration curve is that each box of the biosensors will include an adjustment chip which can supply calibration curve information on the biosensors packed in the box. In this case, the user inserts the adjustment chip into the blood glucose measuring device just the same way as he uses the biosensor. Then, the blood glucose measuring device will automatically select an appropriate calibration curve.

A third example for the selection of the calibration curve is disclosed in the Japanese Patent Laid-Open No. 10-332626. According to the invention disclosed in the gazette, the biosensor is provided with production-lot identifying electrodes separately from concentration level measuring electrodes, and the biosensor outputs signals corresponding to the locations of the production-lot identifying electrodes. The blood glucose measuring device on the other hand has a plurality of determining terminals corresponding to the production-lot identifying electrodes. The blood glucose measuring device uses these determining terminals to pick up the signals corresponding to the locations of the production-lot identifying electrodes, so that the blood glucose measuring device can choose an appropriate calibration curve based on the signals obtained from the biosensor.

However, if the calibration curve selection is relied upon the button operation or the chip insertion to be performed by the user, the user has to do the additional burden of selecting the calibration curve, and even worse is a possibility that the user forgets the operation to select an appropriate curve. If the user forgets the selection of the calibration curve, it becomes impossible to perform blood glucose level measurement truly adjusted for the sensitivity variation of the sensor, etc. Therefore, it is not a good option to depend upon the user in the selection of calibration curve.

Use of the adjustment chip requires a production line for the chips separately from those for the biosensors, which would lead to disadvantages in terms of manufacturing cost.

Use of the production-lot identifying electrodes poses a challenge that the sensitivity of the biosensor must be forecasted and the calibration curve information must be inputted into the biosensor at an early stage of the production. If a large discrepancy is found between the actual sensor sensitivity and the forecast sensitivity, the produced biosensors cannot be distributed through the market, resulting in decreased yield. Thus, there is potential disadvantage in terms of the manufacturing cost.

DISCLOSURE OF THE INVENTION

The present invention was made for a case of analyzing a specimen fluid with an analyzing device capable of selecting a calibration curve, and it is an object of the present invention to provide a cost advantageous method of manufacturing the blood glucose measuring device, as well as making possible to select a calibration curve suitable to the blood glucose measuring device without burden placed onto the user.

An analyzing instrument provided by a first aspect of the present invention includes: a capillary for a sample liquid to move through and stay within the capillary; a sample liquid inlet for introduction of the sample liquid into the capillary; and a liquid introduction regulator for a controlled pattern of the introduction of sample liquid into the capillary.

The analyzing instrument according to the present invention further includes: a common passage in the capillary; and a plurality of individual passages in the capillary connecting to the common passage. In this arrangement, the liquid introduction regulator selects for each of the individual passages whether or not the sample liquid is introduced therein.

The liquid introduction regulator includes, for example, one or more through-holes. When the liquid introduction regulator includes a plurality of through-holes, preferably, each through-hole communicates with a corresponding one of the individual passages. In this arrangement, the liquid introduction regulator selects for each of the individual passages whether or not the sample liquid is introduced therein, by a selection whether or not the corresponding through-hole is opened or closed.

The analyzing instrument according to the present invention further includes a plurality of detecting electrodes each corresponding to one of the individual passages for detection of the introduction of sample liquid into the individual passage. In this arrangement, each through-hole is formed right above the corresponding detecting electrode.

Alternatively, the liquid introduction regulator may select for each of the individual passages whether or not the sample liquid is introduced therein, by a selection of a location at which the corresponding trough-hole is formed. In this arrangement, the analyzing instrument further includes a plurality of detecting electrodes each corresponding to one of the individual passages for detection of the introduction of sample liquid into the individual passage. Each of those through-holes corresponding to the individual passage to which the sample liquid is to be introduced is formed right above the corresponding detecting electrode in order to allow the sample liquid to make contact with the corresponding detecting electrode when the sample liquid is introduced. On the other hand, each of those through-holes corresponding to the individual passage to which the sample liquid is not to be introduced is formed closer to the sample liquid inlet than is an end on the sample liquid inlet side of the corresponding detecting electrode.

In the analyzing instrument according to the present invention, an optical method may be utilized in the detection of the introduction of sample liquid in each of the individual passages.

In the analyzing instrument according to the present invention, the through-holes are formed in a cover for example, laminated to a substrate via a spacer. In this arrangement, the capillary is formed by the substrate, the spacer and the cover.

The spacer preferably includes a recess for formation of an inner space of the capillary, and one or more projections extending toward the sample liquid inlet for formation of the individual passages.

The liquid introduction regulator according to the present invention may alternatively include a through-hole. In this arrangement, the pattern of introduction of the sample liquid is controlled by a selection whether or not the through-hole is opened or closed.

The analyzing instrument according to the present invention may further include one or more detecting electrodes each for detection of the introduction of sample liquid at a location in the capillary. In this arrangement, the liquid introduction regulator includes one or more through-holes communicating with the capillary, and the locations in the capillary to which the sample liquid is to be introduced is selected by a selection of locations at which said one or more through-holes are formed. The liquid introduction regulator may alternatively include one or more detecting electrodes each for detection of the introduction of sample liquid at a location in the capillary. In this arrangement, the liquid introduction regulator includes one or more through-holes communicating with the capillary, and locations in the capillary to which the sample liquid is to be introduced is selected by a selection for each of said one or more through-holes whether the through-hole is opened or closed.

A second aspect of the present invention provides an analyzing device to which an analyzing instrument is attached for analysis of a sample liquid supplied to the analyzing instrument. The analyzing instrument include: a capillary for a sample liquid to move through and stay within the capillary; a sample liquid inlet for introduction of the sample liquid into the capillary; and a liquid introduction regulator for a controlled pattern of the introduction of sample liquid into the capillary. The analyzing device includes a detector for detection of the pattern of introduction of the sample liquid in the capillary.

The analyzing instrument may further includes: one or more detecting electrodes for measurement of an electrical physical quantity for detection purpose as necessary information for the detection of the pattern of introduction of sample liquid in the capillary; and a measuring electrode for measurement of an electrical physical quantity for analysis purpose as necessary information for calculating a concentration of a target component in the sample liquid. In this arrangement, preferably, the analyzing device further includes: a measurer for the measurement of the electrical physical quantity for detection purpose and the electrical physical quantity for analysis purpose; a storage for storage of information about a plurality of calibration curves indicating a relationship between the electrical physical quantity for detection purpose and the concentration level of the target component in sample liquid; a selector for selection of information about a target calibration curve, from the information about the calibration curves; and an arithmetic processor for calculation of the concentration level of the target component based on the electrical physical quantity for analysis purpose and the calibration curve information selected by the selecting means.

The analyzing instrument may further include: a common passage in the capillary; and a plurality of individual passages in the capillary connecting to the common passage. In this arrangement, the detector detects for each of the individual passages whether or not the sample liquid has been introduced therein. On the other hand, each of the detecting electrodes corresponds to one of the individual passages for measurement by the detector of the electrical physical quantity for detection purpose as information necessary for detecting whether or not the sample liquid has been introduced into the individual passage.

The analyzing device according to the present invention further include a plurality of switches for individual selection for each of the detecting electrodes whether to be or not to be electrically conducted with the measurer.

The detector makes a determination for each of the electrical physical quantities obtained by the measurer through the detecting electrode whether or not the quantity has exceeded e.g. a threshold value, thereby making a determination whether or not the sample liquid has been introduced therein for each of the individual passages.

A third aspect of the present invention provides a method of manufacturing an analyzing instrument including: a capillary for a sample liquid to move through and stay within the capillary; a sample liquid inlet for introduction of the sample liquid into the capillary; and a liquid introduction regulator for a controlled pattern of the introduction of sample liquid into the capillary. The method includes a step of filling selected ones of the through-holes in accordance with the pattern of introduction of the sample liquid into the capillary.

If the analyzing instrument further includes: a sample liquid inlet for introduction of the sample liquid into the capillary, a common passage in the capillary; and a plurality of individual passages in the capillary connecting to the common passage, each of the individual passages communicating with a corresponding one of the through-holes in the individual passages; then it is preferable that the step of filling the through-holes includes closing of those through-holes which correspond to those individual passages into which the sample liquid is not to be introduced.

A fourth aspect of the present invention provides a method of manufacturing an analyzing instrument comprising: a capillary for a sample liquid to move through and stay within the capillary; a sample liquid inlet for introduction of the sample liquid into the capillary; a common passage in the capillary; a plurality of individual passages located farther away from the sample liquid inlet than is the common passage and connected to the common passage; and a plurality of through-hole for a selection for each of the individual passages whether to introduce or not to introduce the sample liquid there in. The method includes: a step of forming a first through-hole corresponding to the individual passage into which the sample liquid is not to be introduced, closer to an incoming end of said individual passage for communication with said individual passage; and a step of forming a second through-hole corresponding to the individual passage into which the sample liquid is to be introduced, farther from an incoming end of said individual passage for communicating with said individual passage.

According to a preferred embodiment, the analyzing instrument further includes a plurality of detecting electrodes each corresponding to one of the individual passages for detection of the introduction of the sample liquid into the individual passage, and the first through-hole is formed closer to the incoming end of the individual passage than is an end of the corresponding detecting electrode, whereas the second through-hole is formed right above the corresponding detecting electrode.

BEST MODE FOR CARRYING OUT THE INVENTION

Figure 6:
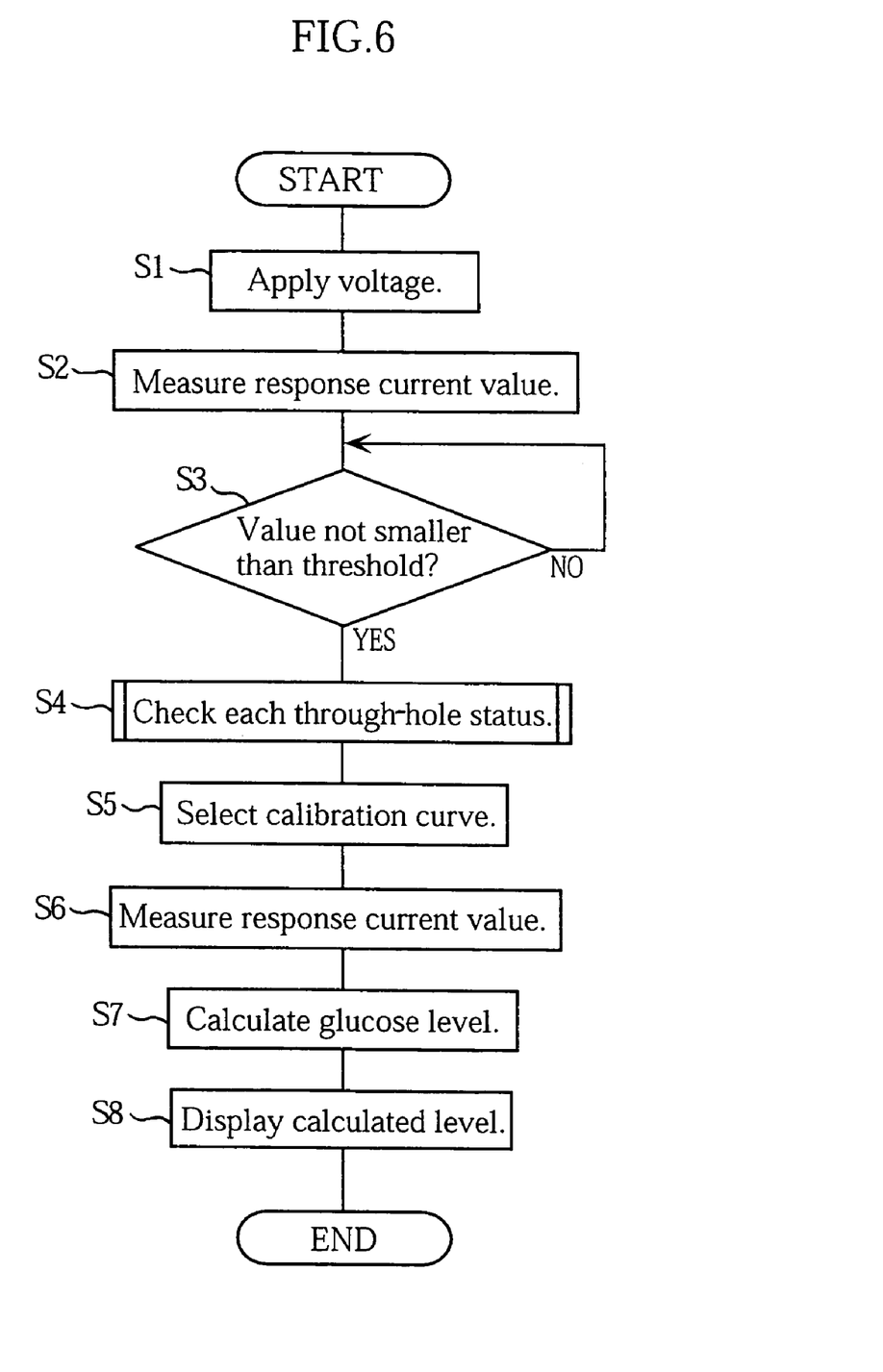
FIG. 6 is a flow chart for illustrating a method of measuring a blood glucose level.
Figure 7:
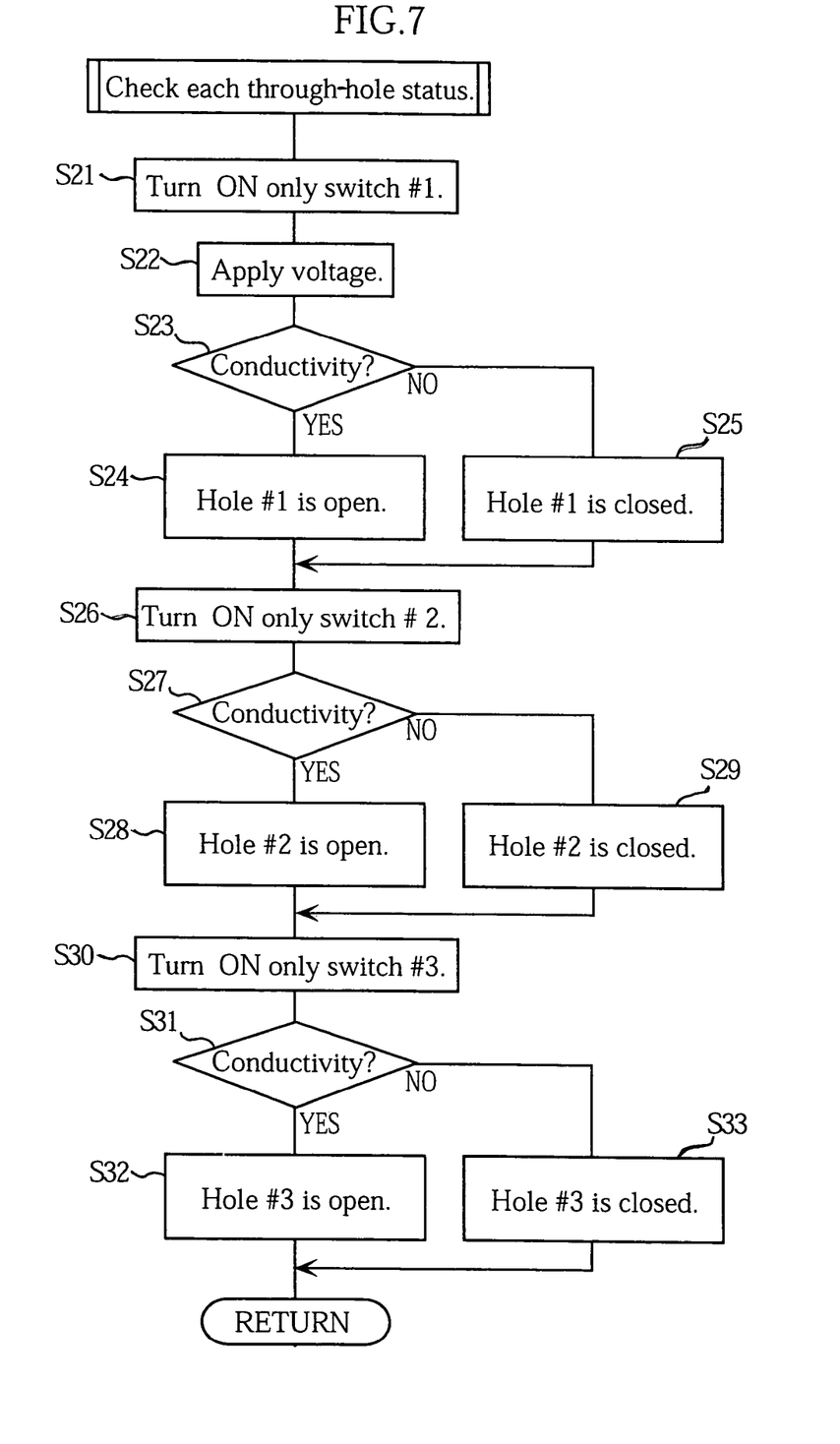
FIG. 7 is a flowchart for illustrating a part of the method of measuring a blood glucose level.

First, a first mode of embodiment of the present invention will be described with reference to FIGS. 1 through 7. FIGS. 1 through 5 are for description of a biosensor and an analyzing device whereas FIGS. 6 and 7 are for description of a method of measuring a blood glucose level with the biosensor and the analyzing device.

Figure 1:
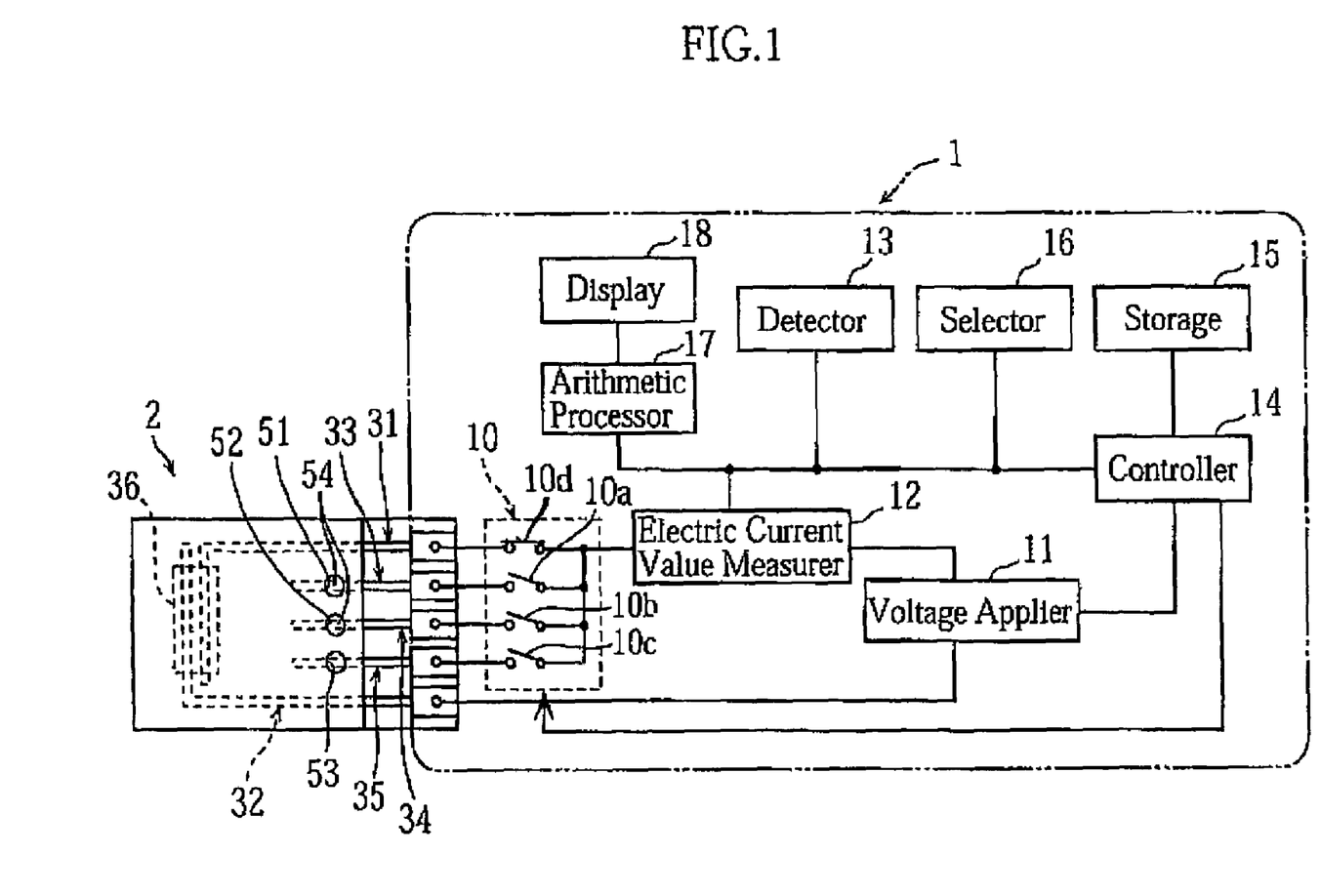
FIG. 1 is a plan view of a biosensor according to a first embodiment of the present invention, as attached to an analyzing device, and a block diagram of the analyzing device.
Figure 2:
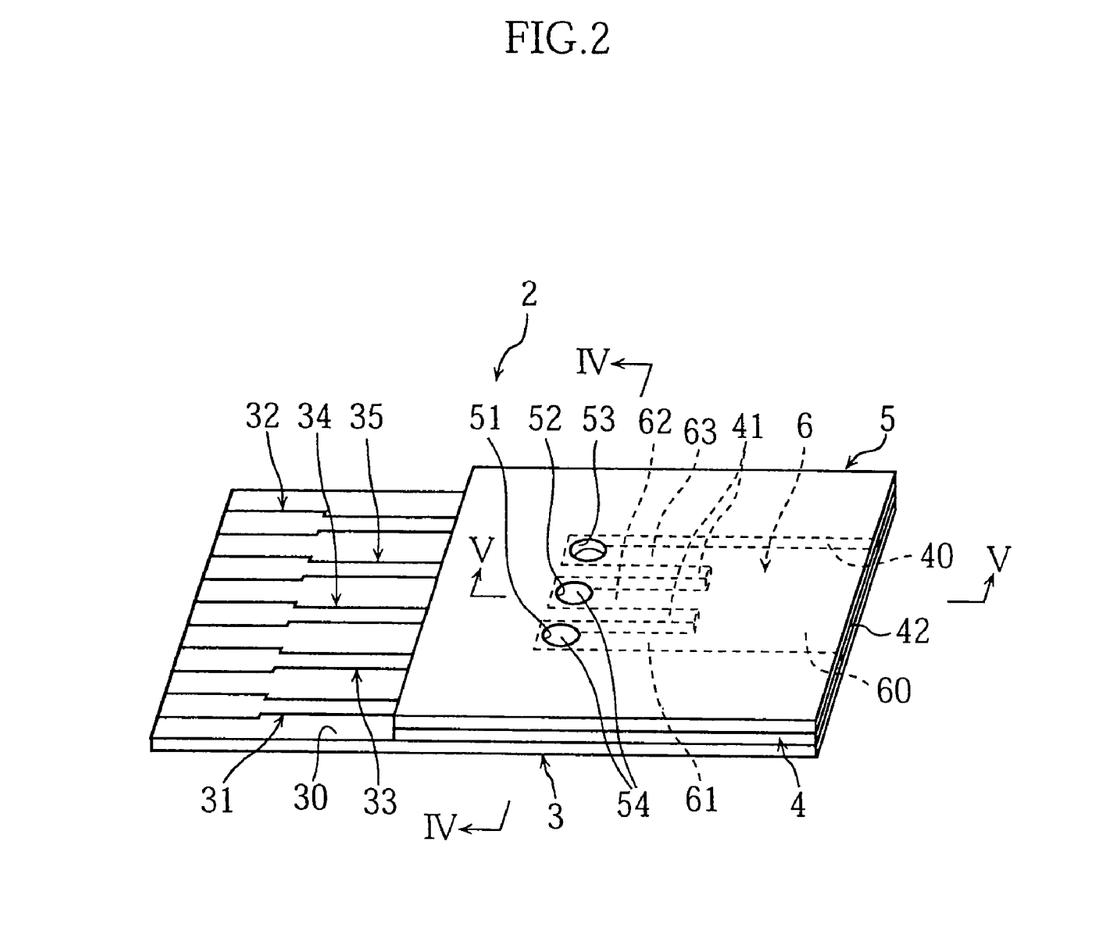
FIG. 2 is an overall perspective view, showing the biosensor in FIG. 1.

As shown in FIG. 1, an analyzing device 1 is a device for analyzing a specific component in a specimen fluid by using a biosensor 2. The analyzing device 1 includes a switcher 10, a voltage applier 11, an electric current value measurer 12, a detector 13, a controller 14, a storage 15, a selector 16, an arithmetic processor 17 and a display 18.

The biosensor 2 is capable of outputting calibration curve information regarding sensitivity of the biosensor 2, and as shown in FIG. 2 through FIG. 5, includes a substrate 3 laminated with a cover 5 via a spacer 4. The biosensor 2 has a capillary 6 formed by the spacer 4 and the cover 5.

Figure 3:
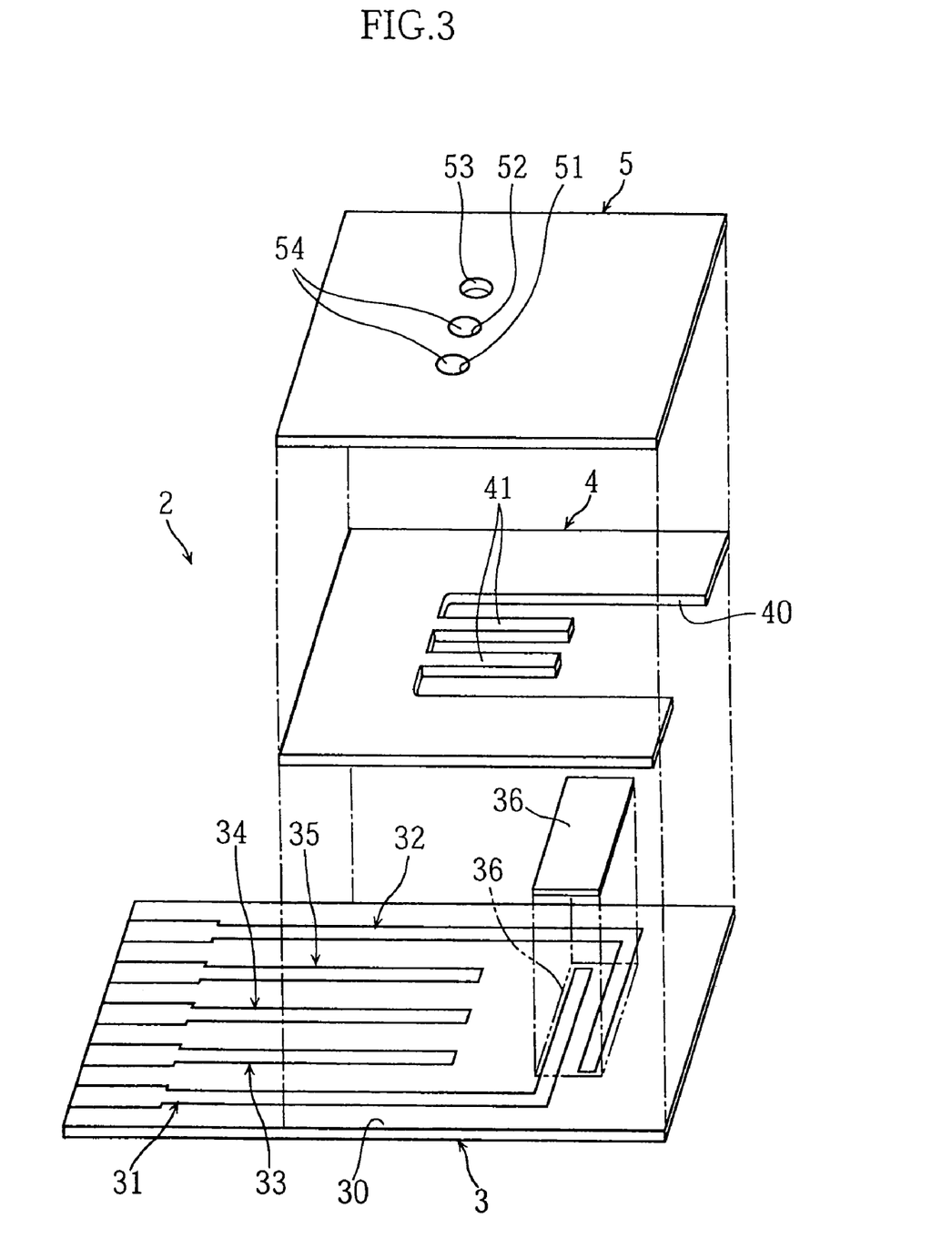
FIG. 3 is an exploded perspective view of the biosensor in FIG. 2.
Figure 4:
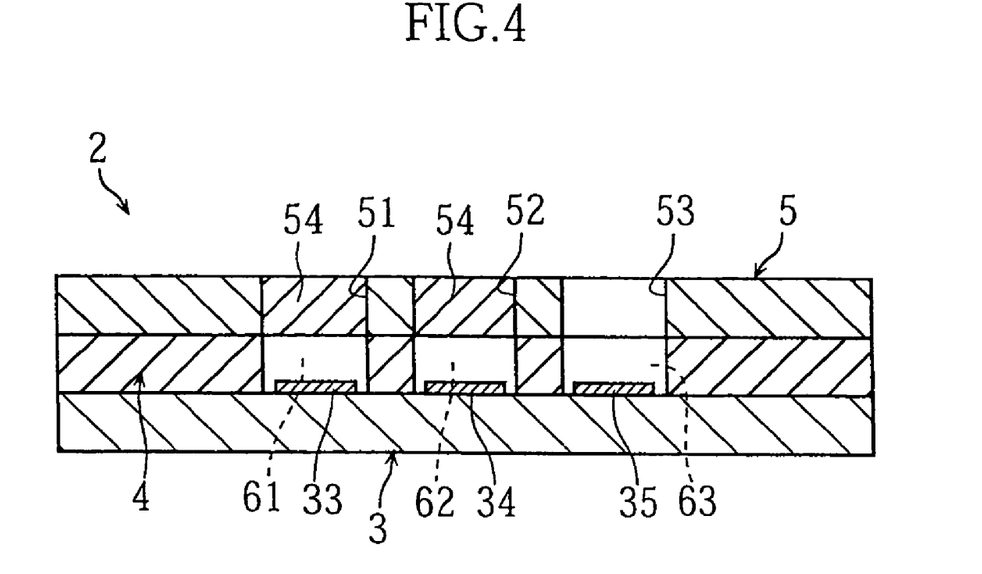
FIG. 4 is a sectional view taken in lines IV—IV in FIG. 2.
Figure 5:
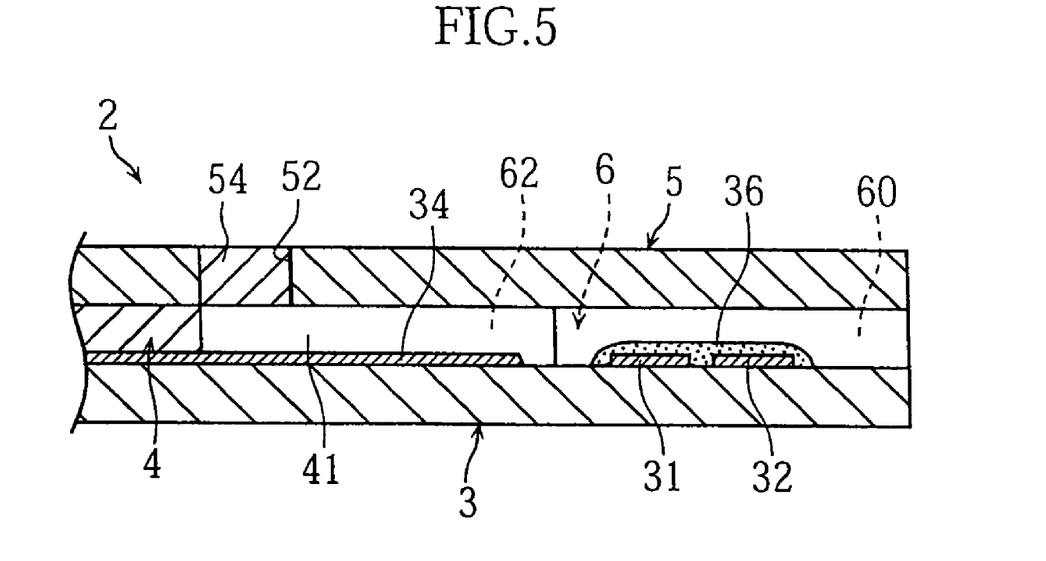
FIG. 5 is a sectional view taken in lines V—V in FIG. 2.

The substrate 3 has an upper surface 30 provided with first and a second measuring electrodes 31, 32, first through third detecting electrodes 33–35, and reactor 36.

The first and second measuring electrodes 31, 32 measure a value of response current necessary for the analysis of the specimen fluid. However, the second measuring electrode 32 is also used when measuring a value of response current necessary for recognition of the calibration curve information, as described later.

The first through third detecting electrodes 33–35 are used together with the second measuring electrode 32 when measuring the value of response current necessary for recognition of the calibration curve information.

The reactor 36 is solid for example, and bridges between the first and the second measuring electrodes 31, 32. The reactor 36 includes, for example, an oxidation-reduction enzyme and an electron transfer material. The oxidation-reduction enzyme and the electron transfer material are selected in accordance with the kind of target component or the object of measurement. For example, when the blood glucose level is measured, the oxidation-reduction enzyme is provided by glucose oxidase or glucose dehydrogenase whereas the electron transfer material is provided by potassium ferricyanide for example.

The spacer 4 has, as clearly shown in FIG. 3, a cutout 40 and two projections 41. The cutout 40 is open to a side and is like comb teeth. The opening in the cutout 40 serves as a sample liquid inlet 42. Each of the projections 41 extends right in front of the first and second measuring electrodes 31, 32, giving the cutout 40 the form of comb teeth, As a result the capillary 6 includes a common passage 60 formed on the sample liquid inlet side, and first through third individual passages 61–63 connecting to the common passage 60.

The cover 5 has first through third through-holes 51–53. Each of the through-holes 51–53 is positionally related to a corresponding one of the first through third individual passages 61–63. Each of the through-holes 51–53 can be fitted with a plug 54 in accordance with the information to be outputted from the biosensor 2. Specifically, by selecting whether to fit or not fit the plug 54 for each of the through-holes 51–53, a selection is made for each of the first through third individual passages 61–63 whether or not communication is made with outside via corresponding one of the through-holes 51–53. In an example shown in FIGS. 2 through 5, the first and second through-holes 51, 52 are fitted with plugs 54, and thus the first and second individual passages 61, 62 do not communicate with the outside. On the other hand, the third through-hole 53 is not fitted with the plug 54, and thus the third individual passage 63 communicates with the outside. It should be noted that the plugs 54 must be made of a non gas-permeable material in order to ensure air-tightness when fitted into the first through third through-holes 51–53.

Alternatively, the through-holes may be sealed with a sheet material, such as an adhesive tape.

In the biosensor 2, since the capillary 6 communicates with the outside via the sample liquid inlet 42 and the third through-hole 53, the sample liquid coming through the sample liquid inlet 42, passes through the common passage 60 by capillarity, and then passes through the third individual passage 63. While flowing through the passages, the sample liquid dissolves the reactor 36, causing for example, an oxidation-reduction enzyme to oxidize a specific component in the sample liquid while reducing the electron transfer material. On the other hand, since the first and second through-holes 51, 52 are fitted with the plugs 54, the sample liquid does not flow into the first and second individual passages 61, 62.

As described, in the biosensor 2, closing or opening the through-holes 51–53 determines whether or not the sample liquid will be introduced into the corresponding individual passages 61–63. As shown in Table 1 below, there are eight possible patterns of the open-close statuses in the first through third through-holes 51–53. However, since it is impossible to introduce the sample liquid into the capillary 6 if all of the first through third through-holes 51–53 are closed, there are seven usable combinations of the open-close statuses in the first through third through-holes 51–53. With this arrangement, by selecting one of the patterns of the open-close statuses of the first through third through-holes 51–53, the biosensor 2 can output a specific kind of target information selected from seven kinds.

TABLE 1

Through-hole Open-Close Status Patterns and Corresponding Calibration Curve Numbers

| 1st Through-hole | 2nd Through-hole | 3rd Through-hole | Calibration Curve No. |
| --- | --- | --- | --- |
| Close | Close | Close | NA |
| Close | Close | Open | 1 |
| Close | Open | Close | 2 |
| Open | Close | Close | 3 |
| Close | Open | Open | 4 |
| Open | Close | Open | 5 |
| Open | Open | Close | 6 |
| Open | Open | Open | 7 |

As shown in Table 1, according to the present embodiment, seven kinds of information outputted from the biosensor 2 are related to seven respective kinds of calibration curve information in order to tune the calculation to the sensitivity of the biosensor 2. Therefore, by having the analyzing device 1 recognize the target information outputted from the biosensor 2, the analyzing device 1 is enabled to perform calculations tuned to the sensitivity of the biosensor 2.

Determining whether the first through third through-holes 51–53 are closed or open, and closing operation of the first through third through-holes 51–53 are done in manufacturing steps of the biosensor 2.

The determination whether the first through third through-holes 51–53 are closed or not is made as follows: First, random sampling is made for biosensors 2 from a given production lot to determine the sensitivity of the biosensor 2. The sensitivity of the biosensor 2 is determined, for example, by measuring an amount of response from the biosensor 2 to a standard sample liquid of a known level of concentration. Next, selection is made for a calibration curve number (information) which will give the most accurate analysis under the given sensitivity of the biosensor 2. Next, in order that the biosensor 2 can output the information representing the calibration curve information, an open-close pattern of the through-holes which represents the calibration curve information is selected, to determine which of the first through third through-holes 51–53 are to be closed. For example, when setting is made for the analyzing device 1 to select a calibration curve corresponding to the calibration curve number 1 in Table 1, determination is made to close the first and second through-holes 51, 52 as shown in FIG. 2 through FIG. 5.

Closing of the first through third through-holes 51–53 is made by fitting the plug(s) 54 into selected through-holes 51–53. For example, when selecting a calibration curve corresponding to calibration curve number 1 in Table 1, the first and second through-holes 51, 52 are fitted with the plugs 54 to make the status shown in FIG. 2 through FIG. 5.

The switcher 10 shown in FIG. 1 has first through fourth switches 10a–10d. The switches 10a–10d are collectively connected to the voltage applier 11 and the electric current value measurer 12 but may be turned on or off by the controller 14 independently from each other. Therefore, by turning on or off each of the switches 10a–10d, selection can be made whether the first measuring electrode 31 and the first through third detecting electrodes 33–35 are electrically connected to the voltage applier 11 and the electric current value measurer 12.

The voltage applier 11 applies a voltage between the first measuring electrode 31 and the second measuring electrode 32, as well as between the first through third detecting electrodes 33–35 and the second measuring electrode 32. The voltage applier 11 is provided by a DC power source such as an ordinary dry battery or a rechargeable battery.

The electric current value measurer 12 measures the value of a response current when the voltage is applied via the voltage applier 11.

The detector 13 detects whether the sample liquid has been introduced into the capillary 6. Specifically, the detector 13 detects if the analysis of the sample liquid is ready to begin since the sample liquid has been introduced into the common passage 60 or if the sample liquid has been introduced into each of the individual passages 61–63.

The controller 14 turns on and off each of the switches 10a–10d, and controls operation of the elements 11, 13, and 15–18, based on a control program stored in the storage 15.

The storage 15 stores the control program for execution by the controller 14, and different kinds of calibration curve information. The calibration curve information sets forth a relationship between the response current values (or voltage values obtained through conversion) and the concentration level of a target component. The calibration curve information is stored in the form of a mathematical formula or table. The storage 15 stores a lookup table like the one shown in Table 1 which indicates a matching relationship between the information outputted from the biosensor 2 and the calibration curve information.

The selector 16 selects appropriate calibration curve information among different kinds of calibration curve information stored in the storage 15, based on the output from the biosensor 2 and the lookup table stored in the storage 15.

The arithmetic processor 17 performs calculations necessary for the analysis of the specific component in the sample liquid, based on the value of a response current measured by the electric current value measurer 12 and the calibration curve information selected by the selector 16.

Each of the detector 13, the controller 14, the storage 15, the selector 16 and the arithmetic processor 17 can be provided by a CPU, a ROM, a RAM or combination thereof. Further, all of these elements can be provided by a single CPU connected to a plurality of memories.

The display 18 displays results of calculations made by the arithmetic processor 17, error messages and so on. The display 18 is provided by a liquid crystal display for example.

Hereinafter, description will be made for a method of measuring a blood glucose level by using the biosensor 2 and the analyzing device 1, with reference to FIG. 1 through FIG. 5 as well as FIG. 6 and FIG. 7. Note that in the analyzing device 1, the fourth switch 10d is turned ON and the first trough third switches 10a–10c are turned OFF while the biosensor 2 is not yet attached.

When measuring the blood glucose level, first, the biosensor 2 is attached to an analyzing device 1, and the blood is introduced into the capillary 6 via the sample liquid inlet 42 of the biosensor 2.

Meanwhile in the analyzing device 1, the controller 14 controls the voltage applier 11 to apply a voltage between the first and second measuring electrodes 31, 32 of the biosensor 2 (S1). At this time, the electric current value measurer 12 measures a value of responding current (S2). The measurements of the responding current value is made per 0.05–0.2 seconds, for example. The detector 13 monitors the responding current values measured at the electric current value measurer 12, and checks if the responding current value is not smaller than a threshold value (S3).

When the detector 13 sees that the responding current value is not smaller than the threshold value (S3: YES), the detector 13 determines that the blood has been introduced into the common passage 60 of the capillary 6. On the other hand, if the detector 13 sees that the responding current value is smaller than the threshold value (S3: NO), the detector 13 goes to Step S3 to continue the check. However, if the detector 13 continues to see the responding current value being smaller than the threshold value after a lapse of a predetermined duration of time (S3: NO), then the program may go to an error processing routine.

When the blood is introduced into the capillary 6, the reactor 36 is dissolved to form a liquid-phase reaction system in the common passage 60. In this liquid-phase reaction system, glucose is oxidized while the electron transfer material is reduced. The electron transfer material is then oxidized when a DC voltage is applied, and a quantity of electrons released can be measured as a responding current value.

When the detector 13 has determined that the responding current value is not smaller than the threshold value (S3: YES), then detection is made for the open-close status of the first through third through-holes 51–53 in the biosensor 2 (S4).

The detection of the open-close status in each of the first through third through-holes 51–53 is made in the following steps as given by a flowchart in FIG. 7.

First, the controller 14 turns ON only the first switch 10a (S21), and have the voltage applier 11 apply a constant voltage between the first detecting electrode 33 and the second measuring electrode 32 (S22). Meanwhile, the detector 13 checks if there is electrical conductivity between the first detecting electrode 33 and the second measuring electrode 32 (S23) based on the measurement result at the electric current value measurer 12.

When there is electrical conductivity between the first detecting electrode 33 and the second measuring electrode 32 (S23: YES), the detector 13 determines that the first through-hole 51 is open (S24). On the contrary, if there is no electrical conductivity between the first detecting electrode 33 and the second measuring electrode 32 (S23: NO), then the detector 13 determines that the first though-hole 51 is closed (S25).

Next by turning ON the second switch 10b only (S26), the detector 13 checks electrical conductivity between the second detecting electrode 34 and the second measuring electrode 32 (S27), to see the open-close status of the second through-hole 52 (S28, S29).

Likewise, by turning ON the third switch 10c only (S30), the detector 13 checks electrical conductivity between the third detecting electrode 35 and the second measuring electrode 32 (S31) to see the open-close status of the third through-hole 53 (S32, S33).

Results of detections on the open-close status at the first through the third through-holes 51–53 are stored in the storage 15.

Next, as shown in FIG. 6, the selector 16 selects a calibration curve that matches the sensitivity of the biosensor 2 (S5) based on the open-close status of the first through third through-holes 51–53. The selection of the calibration curve is made on the basis of a lookup table like Table 1. For example, if the first and the second through-holes 51, 52 are closed and the third through-hole 53 is open, calibration curve information related to the calibration curve number 1 is selected.

Meanwhile, a reference time point is set when the response current value has exceeded the threshold (S3: YES), and upon passing a predetermined time duration (e.g. 5 through 30 seconds), the controller 14 measures a value of response current value using the electric current value measurer 12 (S6), for calculation.

The arithmetic processor 17 calculates a glucose concentration level (S7) based on the calibration curve information selected by the selector 16 and the response current value obtained for the calculation. The result of the calculation is displayed in the display 18 (S8).

With the selection of the open-close status of the first through third through-holes 51–53, the biosensor 2 according to the present embodiment is capable of outputting information correlated to the sensitivity of the biosensor 2. On the other hand, a simple operation of attaching the biosensor 2 makes the analyzing device 1 select a calibration curve which best matches the sensitivity of the biosensor 2 for use in the analysis of the sample liquid. Therefore, since the selection of the calibration curve is performed automatically upon attaching the biosensor 2 to the analyzing device 1 at a time of the analysis of the sample liquid, there is no chance where selection of the calibration curve is forgotten. Thus, it becomes possible to perform appropriate analysis based on a calibration curve which matches the sensitivity of the biosensor 2. Further, there is no need for forcing the user the burden of selecting a calibration curve.

Selection of the open-close status on each of the first through the third through-holes 51–53 of the biosensor 2 can be performed, as has been described, based on actual sensitivity measurement of the biosensor 2 and after the actual measurement. Therefore, the biosensor 2 is provided with information correlated to the sensor sensitivity which appropriately reflects the sensitivity of the biosensor 2, eliminating conventional chances that the actual sensitivity of the sensor is different from forecasts. This eliminates a case that the sensors must be scrapped due to inaccurate forecast, enabling one to improve yield and reduce manufacturing costs.

Figure 8:
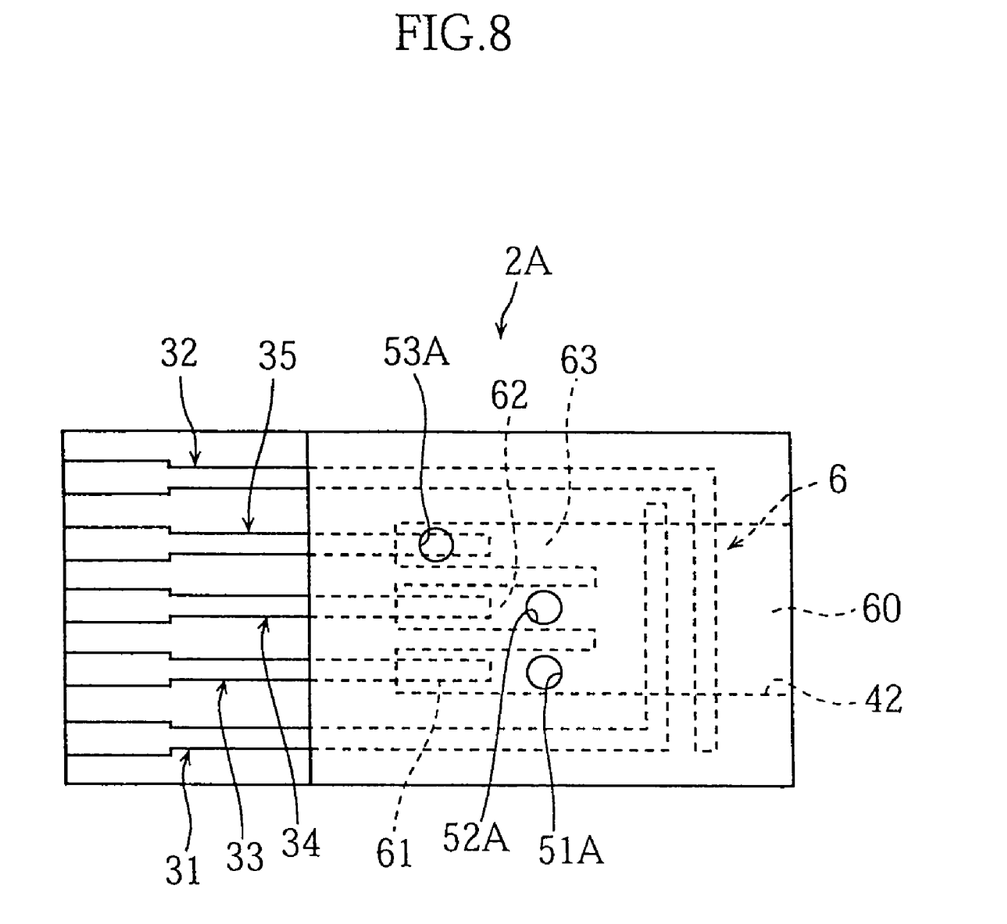
FIG. 8 is a plan view of a biosensor according to a second embodiment of the present invention.

Next, a biosensor according to a second embodiment of the present invention will be described with reference to FIG. 8. A biosensor 2A shown in FIG. 8 uses the same elements as in the biosensor 2 according to the first embodiment. These elements are given identical alpha-numeral codes, and their description will not be repeated hereinafter.

In the biosensor 2A, positions at which the first through third through-holes 51A–53A are formed select whether or not electrical conductivity is established between the second measuring electrode 32 and each of the first through third detecting electrodes 33–35 when the sample liquid is introduced.

In the biosensor 2A, through-holes 51A, 52A which correspond to the first and second detecting electrodes 33, 34 respectively are formed near inlets of the first and second individual passages 61, 62 and closer to the sample liquid inlet 42 than the ends of the first and the second detecting electrode 33, 34. By contrast, a through-hole 53A which corresponds to the third detecting electrode 35 is formed right above the third detecting electrode 35.

Therefore, when the sample liquid is introduced, the sample liquid is not introduced into the first and second individual passages 61, 62, but the liquid is introduced to the third individual passage 63. Thus, the first and the second detecting electrodes 33, 34 do not become conductive with the second measuring electrode 32, while the third detecting electrode 35 becomes conductive with the second measuring electrode 32 when the sample liquid is introduced.

Figure 9:
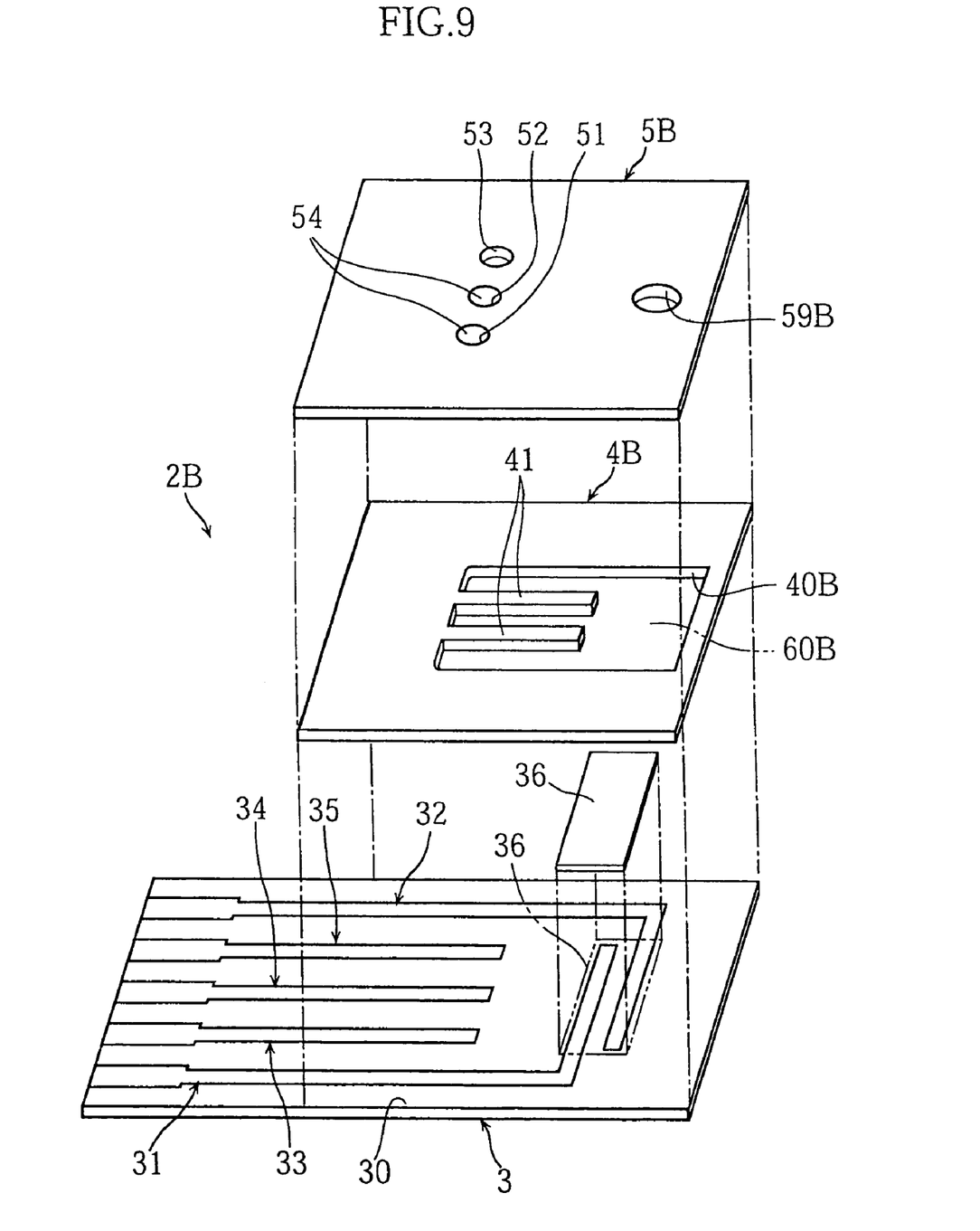
FIG. 9 is an exploded perspective view of a biosensor according to a third embodiment of the present invention.
Figure 10:
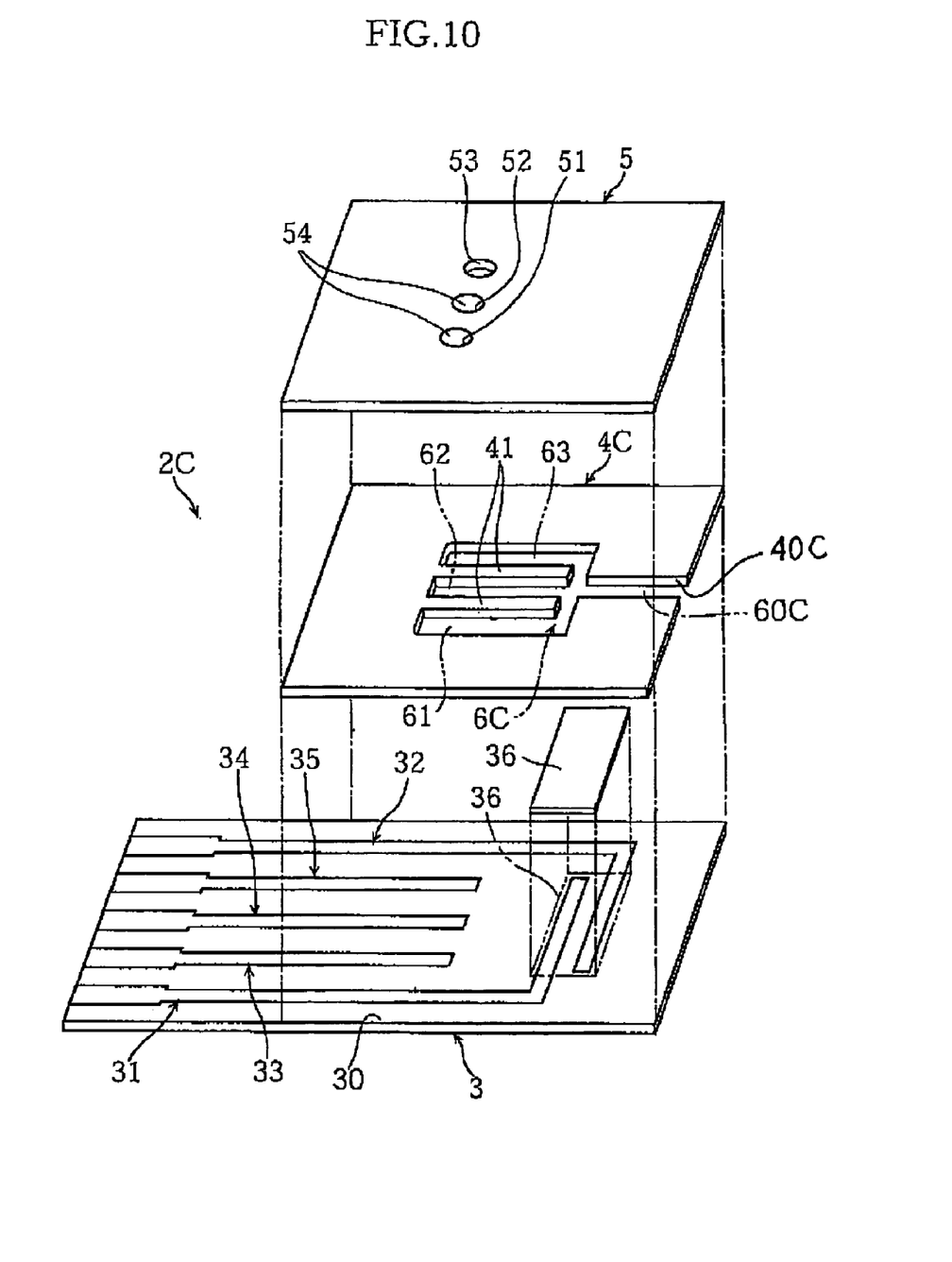
FIG. 10 is an exploded perspective view of a biosensor according to a fourth embodiment of the present invention.

Next, biosensors according to a third and a fourth embodiment of the present invention will be described with reference to FIG. 9 and FIG. 10. FIG. 9 is an exploded perspective view of the biosensor according to the third embodiment, whereas FIG. 10 is an exploded perspective view of the biosensor according to the fourth embodiment. It should be noted that in FIG. 9 and FIG. 10, elements identical with those in the biosensor 2 according to the first embodiment are given identical alpha-numeral codes, and their description will not be repeated hereinafter.

A biosensor 2B shown in FIG. 9 has a cover 5B formed with a through-hole 59B through which the sample liquid is introduced into a common passage 60B. Correspondingly, a spacer 4B is formed with a through-hole 40B instead of the cutout 40 (See FIG. 3) used in the biosensor 2.

On the other hand, a biosensor 2C shown in FIG. 10 has a cutout 40C which differs in shape from the one in the biosensor 2 (See FIG. 1 through FIG. 5). Specifically, a portion serving as a common passage 60C in the spacer 4C has a narrower width. Thus, a capillary 6C takes a form in which individual passages 61–63 branch out of the common passage 60C.

According to the first through fourth embodiments, each individual passage has a corresponding through-hole. Alternatively, the through-holes may be formed only in the individual passages through which the sample liquid is to be introduced. In this ease, the through-holes are formed at a final step of manufacturing the biosensor.

Figure 11:
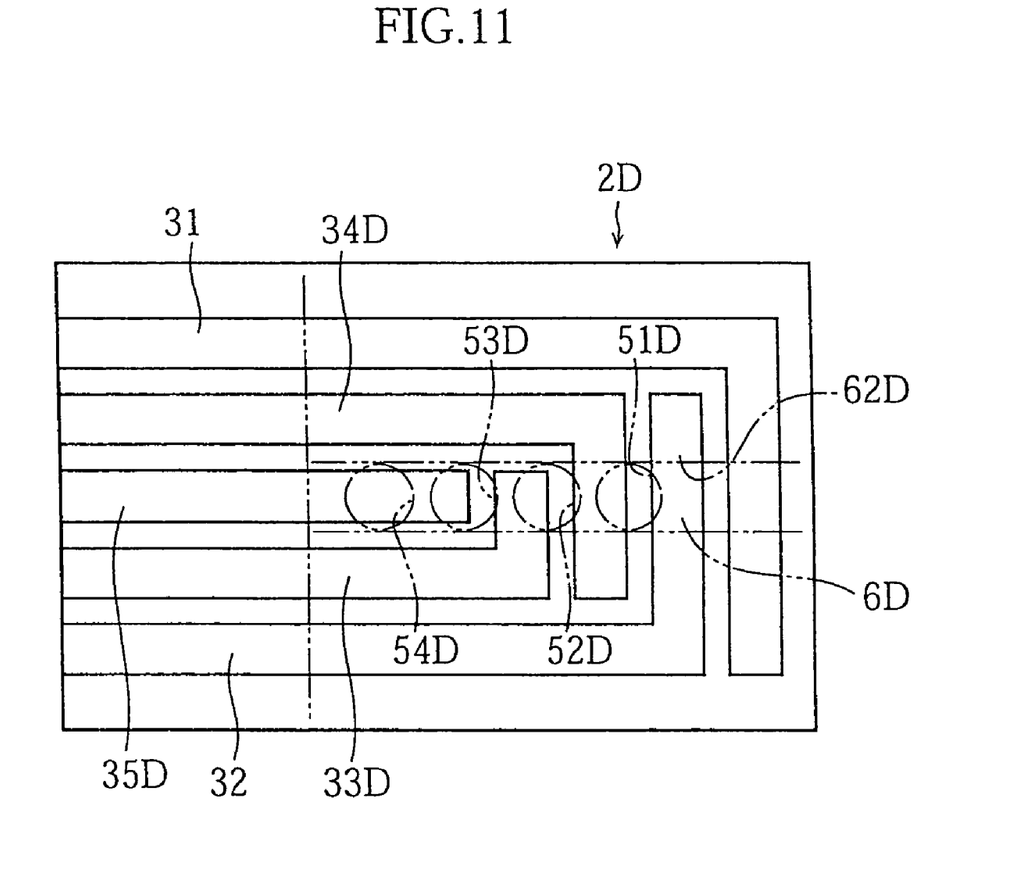
FIG. 11 is a projected plan view of a biosensor according to a fifth embodiment of the present invention.

Next, a fifth embodiment will be described with reference to FIG. 11 and FIG. 12. A biosensor 2D shown in FIG. 11 includes a capillary 6D which has one passage 62D. Ends of the first and second measuring electrodes 31, 32 and of first through third detecting electrodes 33D–35D line up along the capillary 6D, longitudinally of a substrate (enumerated 3D in FIG. 12). A cover (enumerated 5D in FIG. 12), is formed with first through fourth through-holes 51D–54D longitudinally of the substrate 3D. The through-holes 51D–53D can be selectively fitted with plugs 54 depending on the kind of information to be outputted from the biosensor 2D. In other words, by selecting whether to fit or not to fit the through-holes 51D–53D with the plugs 54, selection can be made on the distance in the passage 62D to which the sample liquid is introduced.

Figure 12A:
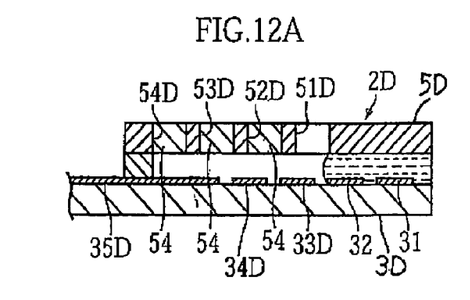
FIG. 12A through FIG. 12D are sectional views for describing a function of the biosensor in FIG. 11.
Figure 12B:
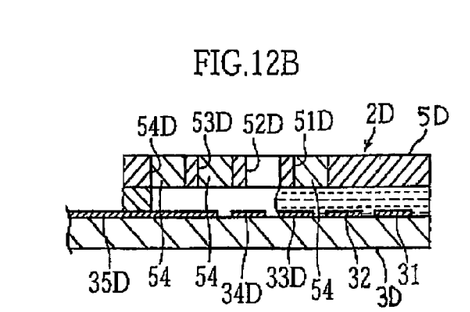
Figure 12C:
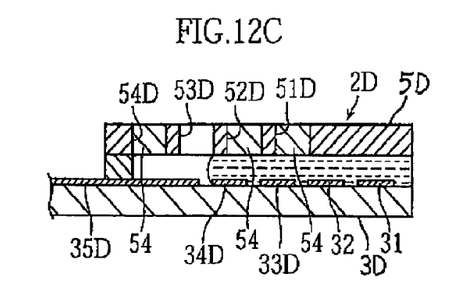
Figure 12D:
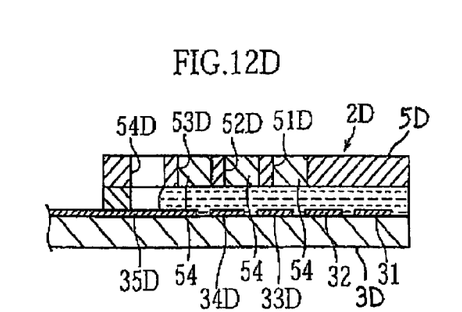

For example, when only the first through-hole 51D is open as shown in FIG. 12A, electrical conductivity is established only between the first and second measuring electrodes 31, 32 when the sample liquid is introduced. Of course, when all of the first through fourth through-holes 51D–54D are open, electrical conductivity is established only between the first and second measuring electrodes 31, 32 when the sample liquid is introduced. FIG. 12B shows a case in which the first through-hole 51D is closed whereas the second through-hole 52D is open: in this case, electrical conductivity is established between the second measuring electrode 32 and the first detecting electrode 33D when the sample liquid is introduced. Of course, when all of the second through fourth through-hole 52D–54D are open, electrical conductivity is established between the second measuring electrode 32 and the first detecting electrode 33D when the sample liquid is introduced. FIG. 12C shows a case in which the first and second through-holes 51D, 52D are closed whereas the third through-hole 53D is open: in this case, electrical conductivity is established between the second measuring electrode 32 and the second detecting electrode 34D when the sample liquid is introduced. Of course, when the third and fourth through-holes 53D, 54D are open, electrical conductivity is established between the second measuring electrode 32 and the second detecting electrode 34D when the sample liquid is introduced. FIG. 12D shows a case in which the fist through third through-holes 51D–53D are closed whereas the fourth through-holes 54D is open: in this case, electrical conductivity is established between the second measuring electrode 32 and the third detecting electrode 35D when the sample liquid is introduced.

As described above, according to the biosensor 2D, it is possible to have the analyzing device recognize one of the four kinds of calibration curve information in order to select the target calibration curve, as shown in Table 2.

TABLE 2

Through-hole Open-Close Status Patterns and Corresponding Calibration Curve Numbers

| 1st Through-hole | 2nd Through-hole | 3rd Through-hole | 4th Through-hole | Calibration Curve No. |
| --- | --- | --- | --- | --- |
| Open | Close (Open) | Close (Open) | Close (Open) | 1 |
| Close | Open | Close (Open) | Close (Open) | 2 |
| Close | Close | Open | Close (Open) | 3 |
| Close | Close | Close | Open | 4 |

According to the present embodiment, a plurality of through-holes are formed in advance, so that selected through-holes are closed with plugs. Alternatively, the through-holes may be formed only at selected locations so that the sample liquid will reach a desired distance in the capillary. Further, in the first through fourth embodiments, the individual passages may use a similar arrangement as in the fifth embodiment.

The present invention is not limited to the embodiments so far described. For example, the number of through-holes, individual passages and detecting electrodes in the biosensor is not limited to those illustrated in the drawings.

The invention claimed is:
1. An analyzing instrument comprising:
a capillary for moving and retaining a sample liquid;
a sample liquid inlet for introduction of the sample liquid into the capillary;
measuring electrodes for measuring a target component in the sample liquid;
liquid introduction regulator for controlled introduction of the sample liquid into the capillary; and one or more detecting electrodes provided separately from the measuring electrodes for detecting the controlled introduction of the sample liquid into the capillary.

2. The analyzing instrument according to claim 1, further comprising:
a common passage in the capillary; and
a plurality of individual passages in the capillary connecting to the common passage,
wherein the liquid introduction regulator determines for each of the individual passages whether or not the sample liquid is introduced therein.

3. The analyzing instrument according to claim 2, wherein the liquid introduction regulator includes one or more through-holes.

4. The analyzing instrument according to claim 2, wherein the liquid introduction regulator includes a plurality of through-holes,
each through-hole communicating with a corresponding one of the individual passages.

5. The analyzing instrument according to claim 4, wherein the liquid introduction regulator determines for each of the individual passages whether or not the sample liquid is introduced therein, by determining whether or not the corresponding through-hole is opened or closed.

6. The analyzing instrument according to claim 5, wherein each of the plurality of detecting electrodes corresponding to one of the individual passages for detection of the introduction of the sample liquid into the individual passage,
wherein each through-hole is right above the corresponding detecting electrode.

7. The analyzing instrument according to claim 4, wherein the liquid introduction regulator determines for each of the individual passages whether or not the sample liquid is introduced therein, by determining a location at which the corresponding through-hole is formed.

8. The analyzing instrument according to claim 7, wherein each of said one or more detecting electrodes corresponds to one of the individual passages for detection of the introduction of the sample liquid into the individual passage,
wherein each of those through-holes corresponding to the individual passage to which the sample liquid is to be introduced is right above the corresponding detecting electrode,
each of those through-holes corresponding to the individual passage to which the sample liquid is not to be introduced being closer to the sample liquid inlet than is an end on the sample liquid inlet side of the corresponding detecting electrode.

9. The analyzing instrument according to claim 4, wherein the through-holes are formed in a cover laminated to a substrate via a spacer.

10. The analyzing instrument according to claim 2, wherein the capillary is formed by a substrate, a spacer and a cover laminated to the substrate via the spacer,
the spacer including a recess for formation of an inner space of the capillary, and one or more projections extending toward the sample liquid inlet for formation of the individual passages.

11. The analyzing instrument according to claim 1, wherein the sample liquid inlet includes a through-hole, the introduction of the sample liquid being regulated by determining whether or not the through-hole is opened or closed.

12. The analyzing instrument according to claim 1, wherein
the liquid introduction regulator includes one or more through-holes communicating with the capillary, locations in the capillary to which the sample liquid is to be introduced being determined by locations at which said one or more through-holes are formed.

13. The analyzing instrument according to claim 1,
wherein the liquid introduction regulator includes one or more through-holes communicating with the capillary, locations in the capillary to which the sample liquid is to be introduced being determined by whether each of said one or more through-holes is opened or closed.

14. An analyzing device to which an analyzing instrument is attached for analysis of a sample liquid supplied to the analyzing instrument,
the analyzing instrument including: a capillary for moving and retaining a sample liquid; a sample liquid inlet for introduction of the sample liquid into the capillary; measuring electrodes for measuring a specific component of the sample liquid; a liquid introduction regulator for controlled introduction of the sample liquid into the capillary; one or more detecting electrodes provided separately from the measuring electrodes for detecting the controlled introduction of the sample liquid into the capillary,
the analyzing device including a detector connected to said one or more detecting electrodes for detection of the controlled introduction of the sample liquid in the capillary.

15. The analyzing device according to claim 14, wherein said one or more detecting electrodes measure an electrical physical quantity for detection purpose as necessary information for the detection of the controlled introduction of the sample liquid in the capillary; and the measuring electrodes measure an electrical physical quantity for analysis purpose as necessary information for calculating a concentration of the target component in the sample liquid,
to analyzing device further comprising:
a measurer for the measurement of the electrical physical quantity for detection purpose and the electrical physical quantity for analysis purpose;
a storage for storing information about a plurality of calibration curves indicating a relationship between the electrical physical quantity for detection purpose and the concentration of the target component in the sample liquid;
a selector for selection of a target calibration curve, from the plurality of calibration curves; and
an arithmetic processor for calculation of the concentration of the target component based on the electrical physical quantity for analysis purpose and the calibration curve selected by the selector.

16. The analyzing device according to claim 15,
wherein the analyzing instrument further includes: a common passage in the capillary; and a plurality of individual passages in the capillary connecting to the common passage, and
wherein the detector detects for each of the individual passages whetter or not the sample liquid has been introduced therein.

17. The analyzing device according to claim 16, wherein each of said one or more detecting electrodes corresponds to one of the individual passages for measurement by the detector of the electrical physical quantity for detection purpose as information necessary for detecting whether or not the sample liquid has been introduced into the individual passage.

18. The analyzing device according to claim 17, wherein the detector makes a determination for each of the electrical physical quantities obtained by the measurer through said one or more detecting electrodes whether or not the quantity has exceeded a threshold value, thereby making a determination whether or not the sample liquid has been introduced for each of the individual passages.

19. The analyzing device according to claim 15, further comprising a plurality of switches for selectively connecting each of said one or more detecting electrodes with the measurer.

20. A method of manufacturing an analyzing instrument comprising: a capillary for moving and retaining a sample liquid; and a plurality of through-holes for controlled introduction of the sample liquid into the capillary,
the method including a step of selectively closing the through-holes for providing the controlled introduction of the sample liquid into the capillary.

21. The method of manufacturing the analyzing instrument according to claim 20,
wherein the analyzing instrument further includes: a sample liquid inlet for introduction of the sample liquid into the capillary, a common passage in the capillary; and a plurality of individual passages in the capillary connecting to the common passage, each of the individual passages communicating with a corresponding one of the through-holes in the individual passages, and
wherein the step of selectively closing the through-holes includes closing of those through-holes which correspond to those individual passages into which the sample liquid is not to be introduced.

22. A method of manufacturing an analyzing instrument comprising: a capillary for moving and retaining a sample liquid; a sample liquid inlet for introduction of the sample liquid into the capillary; a common passage in the capillary; a plurality of individual passages located farther away from the sample liquid inlet than is the common passage and connected to the common passage; and a plurality of through-holes for determining for each of the individual passages whether to introduce or not to introduce the sample liquid there in; the method including:
a step of forming a first through-hole corresponding to one of the individual passages into which the sample liquid is not to be introduced, closer to an incoming end of said one individual passage for communication with said one individual passage; and
a step of forming a second through-hole corresponding to another of the individual passages into which the sample liquid is to be introduced, farther from an incoming end of said individual passage for communicating with said another individual passage.

23. The method of manufacturing the analyzing instrument according to claim 22, wherein
the analyzing instrument further comprising a plurality of detecting electrodes each corresponding to one of the individual passages for detection of the introduction of the sample liquid into the individual passage,
the first through-hole being formed closer to the incoming end of the individual passage than is an end of the corresponding detecting electrode,
the second through-hole being formed right above the corresponding detecting electrode.

* * * * *